US00PP21941P2

(12) United States Plant Patent
Garcia

(10) Patent No.: US PP21,941 P2
(45) Date of Patent: May 31, 2011

(54) ***ILEX* PLANT NAMED 'MONNIEVES'**

(50) Latin Name: *Ilex×meservae*
Varietal Denomination: Monnieves

(75) Inventor: Nieves Garcia, McMinnville, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 12/660,954

(22) Filed: Mar. 8, 2010

(51) Int. Cl.
*A01H 5/00* (2006.01)

(52) U.S. Cl. ..... Plt./247

(58) Field of Classification Search ..... Plt./247
See application file for complete search history.

*Primary Examiner* — Annette H Para
(74) *Attorney, Agent, or Firm* — C. A. Whealy

(57) ABSTRACT

A new and distinct cultivar of *Ilex* plant named 'Monnieves', characterized by its compact, upright and open plant form; freely branching habit; vigorous growth habit; dark burgundy-colored developing stems; dark green-colored leaves; and good garden performance.

1 Drawing Sheet

Botanical designation: *Ilex×meservae.*
Cultivar denomination: 'MONNIEVES'.

BACKGROUND OF THE INVENTION

The present Invention relates to a new and distinct *Ilex* plant, botanically known as *Ilex×meservae,* and hereinafter referred to by the name 'Monnieves'.

The new *Ilex* plant is a naturally-occurring whole plant mutation of *Ilex×meservae* 'Mondo', disclosed in U.S. Plant Pat. No. 9,999. The new *Ilex* plant was discovered by the Inventor in 2002 from within a population of plants of 'Mondo' in a controlled outdoor nursery environment in Dayton, Oreg.

Asexual reproduction of the *Ilex* plant by cuttings in Dayton, Oreg. since August, 2004, has shown that the unique features of this new *Ilex* plant are stable and reproduced true to type in successive generations of asexual reproduction.

SUMMARY OF THE INVENTION

Plants of the new *Ilex* have not been observed under all possible environmental conditions. The phenotype may vary somewhat with variations in environment such as temperature and/or light intensity without, however, any variance in genotype. The following traits have been repeatedly observed and are determined to be the unique characteristics of 'Monnieves'. These characteristics in combination distinguish 'Monnieves' as a new and distinct cultivar of *Ilex:*

1. Compact, upright and open plant form.
2. Freely branching habit.
3. Vigorous growth habit.
4. Dark burgundy-colored developing stems.
5. Dark green-colored leaves.
6. Good garden performance.

Plants of the new *Ilex* can be compared to plants of the parent, 'Mondo'. Plants of the new *Ilex* differ from plants of 'Mondo' in the following characteristics:

1. Plants of the new *Ilex* are taller and narrower than plants of 'Mondo'.
2. Plants of the new *Ilex* are more upright than and not as rounded as plants of 'Mondo'.

3. Plants of the new *Ilex* are more open than and not as dense as plants of 'Mondo'.
4. Plants of the new *Ilex* and 'Mondo' differ slightly in stem and leaf color.
5. Plants of the new *Ilex* are not susceptible to *Phytophthora* whereas plants of 'Mondo' are susceptible to *Phytophthora.*

Plants of the new *Ilex* can be compared to the plants of *Ilex×meservae* 'Blue Baron', disclosed in U.S. Plant Pat. No. 16,151. In side-by-side comparisons conducted in Dayton, Oreg., plants of the new *Ilex* differed from plants of 'Blue Baron' in the following characteristics:

1. Plants of the new *Ilex* are not as broad as plants of 'Blue Baron'.
2. Plants of the new *Ilex* have shorter and narrower leaves than plants of 'Blue Baron'.

BRIEF DESCRIPTION OF THE PHOTOGRAPHS

The accompanying colored photographs illustrate the overall appearance of the new *Ilex* plant. These photographs show the colors as true as it is reasonably possible to obtain in colored reproductions of this type. Colors in the photographs may differ slightly from the color values cited in the detailed botanical description, which accurately describe the colors of the new *Ilex* plant. The photograph at the bottom of the sheet comprises a side perspective view of a typical plant of 'Monnieves' grown in a container. The photograph at the top of the sheet is a close-up view of a typical plant of 'Monnieves'.

DETAILED BOTANICAL DESCRIPTION

The aforementioned photographs and following observations and measurements describe plants grown in three-gallon containers during the winter in Dayton, Oreg. in an outdoor nursery and under commercial production conditions. During the production of the plants, day temperatures averaged 4° C. and night temperatures averaged −5° C. Plants used for the photographs and description were 42 months old. In the following description, color references are made to The Royal Horticultural Society Colour Chart, 2007 Edition, except where general terms of ordinary dictionary significance are used.

Botanical classification: *Ilex×meservae* 'Monnieves'.

Parentage: Naturally-occurring whole plant mutation of *Ilex× meservae* 'Mondo', disclosed in U.S. Plant Pat. No. 9,999.

Propagation:

*Type.*—By cuttings.

*Time to initiate roots.*—About 21 to 30 days at temperatures of 20° C.

*Time to produce a rooted young plant.*—About three months at temperatures of 20° C.

*Root description.*—Fine, fleshy; off-white in color.

*Rooting habit.*—Moderately freely branching; moderately dense.

Plant description:

*Plant form and growth habit.*—Perennial evergreen shrub; compact upright and open plant form; vigorous growth habit.

*Branching habit.*—Freely branching habit; bushy growth habit with eight primary lateral branches each with multiple secondary lateral branches developing per plant.

*Plant height.*—About 50 cm.

*Plant diameter, area of spread.*—About 41 cm.

*Lateral branch description.*—Length: About 39 cm. Diameter: About 6 mm to 9 mm. Internode length: About 1.1 cm. Strength: Strong. Texture: Smooth, glabrous. Color, young stems: Close to 187B to 187A. Color, mature stems: Close to 147A.

*Foliage description.*—Arrangement: Alternate, simple. Length: About 3.5 cm. Width: About 2.7 cm. Shape: Elliptic to slightly rounded. Apex: Acute. Base: Attenuate. Margin: Broadly serrate. Venation pattern: Pinnate, reticulate. Texture, upper and lower surfaces: Smooth, glabrous. Color: Developing leaves, upper surface: Slightly darker than N137A; towards the apex and margins, close to 200B. Developing leaves, lower surface: Close to N199A. Fully expanded leaves, upper surface: Darker and brighter than 147A; venation, close to 147B. Fully expanded leaves, lower surface: Close to 146C; venation, close to 146B. Petiole: Length: About 8 mm. Diameter: About 1 mm. Texture, upper and lower surfaces: Smooth, glabrous. Color, upper surface: Close to N199A. Color, lower surface: Close to N199B.

Flower description: Flower initiation and development have not been observed on plants of the new *Ilex*.

Garden performance: Plants of the new *Ilex* have been observed to have good garden performance and to tolerate rain, wind and temperatures ranging from about −10° C. to about 43° C.

Disease/pest resistance: Plants of the new *Ilex* are not susceptible to *Phytophthora*. Plants of the new *Ilex* have not been observed to be resistant to pests and other pathogens common to *Ilex*.

It is claimed:

1. A new and distinct cultivar of *Ilex* plant named 'Monnieves' as illustrated and described.

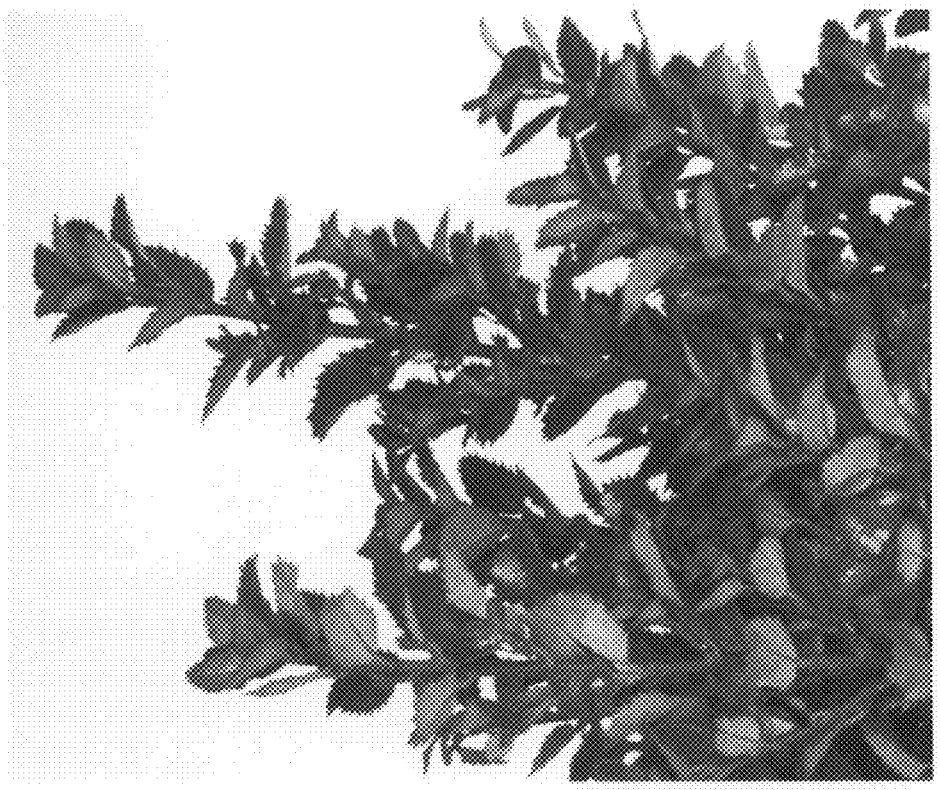
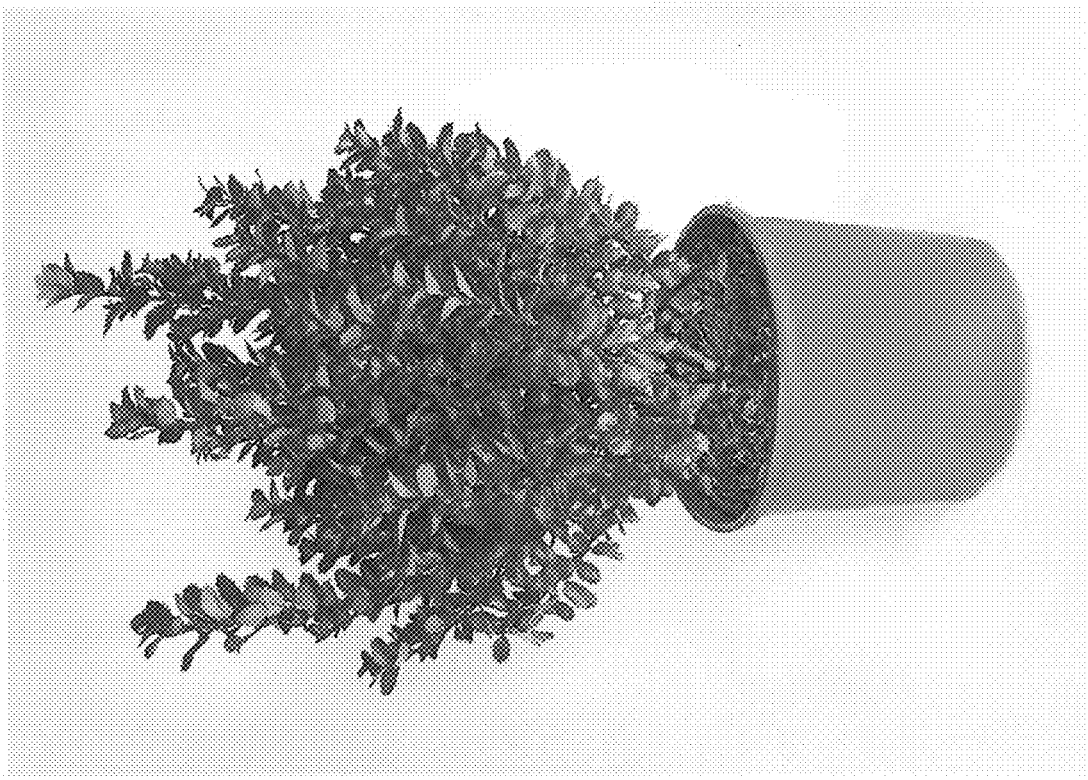

* * * * *